United States Patent [19]
Barbosa et al.

[11] Patent Number: 6,063,578
[45] Date of Patent: May 16, 2000

[54] DUAL REPORTER SYSTEM AND METHODS OF USE THEREFOR

[75] Inventors: Miguel Barbosa; Graham K. Bilter, both of San Diego; Robert Kovelman, La Jolla, all of Calif.

[73] Assignee: Signal Pharmaceuticals, Inc., San Diego, Calif.

[21] Appl. No.: 09/177,785

[22] Filed: Oct. 22, 1998

[51] Int. Cl.[7] .............................. C12Q 1/68; C12N 5/10; C12N 15/85

[52] U.S. Cl. .......................... 435/6; 435/320.1; 435/366; 435/371

[58] Field of Search .......................... 435/6, 320.1, 325, 435/366, 371

[56] References Cited

U.S. PATENT DOCUMENTS

| | | | |
|---|---|---|---|
| 5,620,849 | 4/1997 | Botchan et al. | 435/6 |
| 5,928,888 | 7/1999 | Whitney | 435/29 |
| 5,965,393 | 10/1999 | Hasnain et al. | 435/69.1 |

OTHER PUBLICATIONS

Breiding et al., "Functional Interaction of a Novel Cellular Protein with the Papillomavirus E2 Transactivation Domain," *Molecular And Cellular Biology 17*(12): 7208–7219, 1997.

Ferguson and Botchan, "Genetic Analysis of the Activation Domain of Bovine Papillomavirus Protein E2: Its Role in Transcription and Replication," *Journal Of Virology 70*(7): 4193–4199, 1996.

Frattini and Lamins, "The Role of the E1 and E2 Proteins in the Replication of Human Papillomavirus Type 31b," *Virology 204*: 799–804, 1994.

Huang et al., "Potential Replication of Recombinant Baculoviruses in Nontarget Insect Species: Reporter Gene Products as Indicators of Infection," *Journal Of Invertebrate Pathology 69*: 234–245, 1997.

Lambert, "Papillomavirus DNA Replication," *Journal Of Virology 65*(7): 3417–3420, 1991.

Monini et al., "Activation of Eukaryotic Transcriptional Prometers by the Bovine Papillomavirus E1–Replication Factor," *Intervirology 36*: 245–252, 1993.

Powell et al., "Inhibition of cellular activation of retroviral replication by CD8[+] T cells derived from non–human primates," *Clin. Exp. Immunol. 91*: 473–481, 1993.

Ustav and Stenlund, "Transient replication of BPV–1 requires two viral polypeptides encoded by the E1 and E2 open reading frames," *The EMBO Journal 10*(2): 449–457, 1991.

*Primary Examiner*—Robert A. Schwartzman
*Attorney, Agent, or Firm*—Seed I.P. Law Group PLLC

[57] ABSTRACT

Plasmid reporter systems for assaying transcription and replication are provided. The plasmids comprise dual reporters for use in the independent evaluation of transcription and replication. Such plasmids may be used for example, for determining the role of endogenous factors in transcription and replication and for evaluating the effect of exogenous modulators on such processes. Within certain embodiments, the plasmids comprise (a) a first reporter gene operably linked to a promoter and a binding site for human papillomavirus E1 and/or E2 protein; (b) a second reporter gene that is linked to a promoter that is not substantially modulated by E1 and/or E2 and (c) an origin of replication bound by human papillomavirus E1 protein.

40 Claims, 8 Drawing Sheets

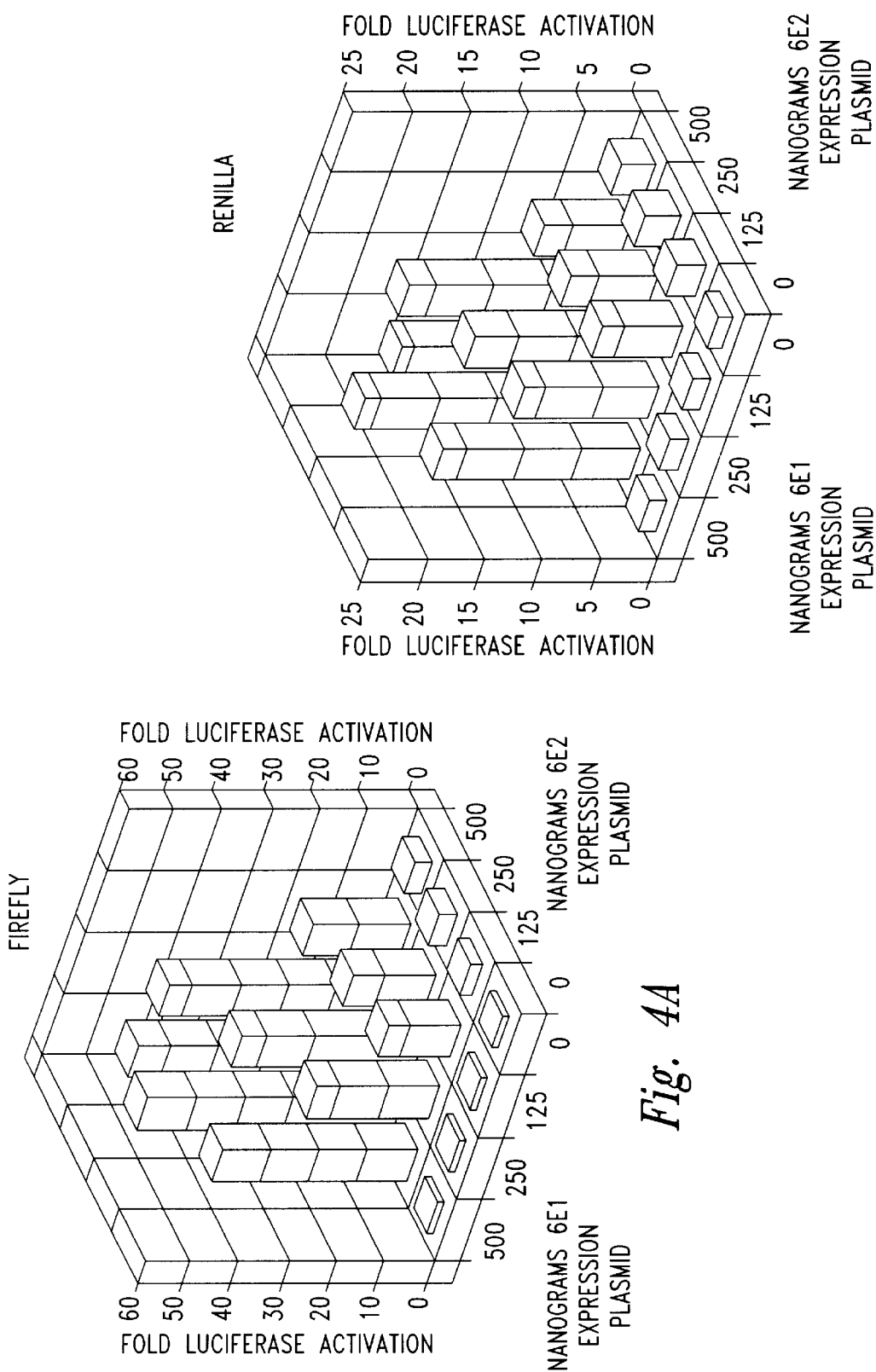

DUAL REPORTER SYSTEM AND METHODS OF USE THEREFOR

TECHNICAL FIELD

The present invention relates generally to systems for independently evaluating effects on DNA transcription and replication. The invention is more particularly related to plasmid systems for use in assaying the ability of proteins and other agents to modulate transcription and replication.

BACKGROUND OF THE INVENTION

Many viral proteins are involved in the regulation of viral genome replication or gene transcription, and some proteins play a role in both processes To facilitate the development of effective therapies based on such proteins, it is necessary to distinguish between effects on gene transcription and replication. Current systems employed for such assays evaluate effects on replication using hybridization or amplification techniques for directly assessing the level of plasmid in a cell sample. Such techniques involve plasmid isolation and digestion, and are too time-consuming and costly for most routine screening purposes. Other techniques employ separate plasmids, each containing a reporter gene, but such systems do not reflect the natural environment and are limited in the ability to assess the two processes, since replication of the two plasmids is fully independent.

One pathogen that employs proteins that modulate both transcription and replication is the papillomavirus. Human papillomaviruses (HPVs) infect squamous epithelial cells, and can induce a variety of benign papillomas or neoplasias. Certain HPV types are commonly associated with benign genital warts, which rarely progress to cancer. However, other HPV types are associated with intraepithelial neoplastic lesions that can progress to malignancies. There is currently no adequate treatment or preventive therapy for such conditions.

The life cycle of HPV can generally be divided into three phases. In the first phase, HPV infects basal cells and the viral genome is established as a stable, low-copy episome. In the second phase, the viral genome is maintained at 50–100 copies per cell, and replicates with the cellular DNA. During the third phase the infected cells undergo differentiation and the viral genome is amplified to several thousand copies per cell. Viral late gene expression is also induced at this time.

To facilitate the development of improved therapies for HPV-associated conditions, it is necessary to gain a further understanding of the molecular mechanisms that regulate events in each phase of the HPV life cycle. Studies to date have identified two proteins, E1 and E2, which are required for viral replication and gene transcription (see Ustav and Stenlund, *EMBO J*. 10:449–457, 1991). E1 is a 73 kD protein that binds ATP and the HPV origin of replication, and exhibits helicase and origin unwinding activities (see, e.g., Blitz and Laimins, *J. Virol*. 65:649–656, 1991; Lambert, *J. Virol*. 65:3417–3420, 1991). E2 is a 42 kD transcriptional activator that binds to the sequence (ACCN$_6$GGT; SEQ ID NO: 1) and also forms a complex with E1. However, as a result of this complex formation, and because these proteins appear to have multiple functions, the specific roles of each protein in the HPV life cycle remain unclear. Further work needs to be performed to understand the roles of E1. E2 and other proteins in the regulation of HPV transcription and replication and to identify agents that modulate the activity of such proteins. Such studies have been hampered by the lack of an in vitro system for the separate evaluation of both processes.

Accordingly, there is a need in the art for a system that permits independent assay of transcription and replication, particularly for viral systems. The present invention fulfills this need and further provides other related advantages.

SUMMARY OF THE INVENTION

Briefly stated, the present invention provides plasmid systems comprising dual reporters for use in the independent evaluation of transcription and replication. Within certain aspects, methods are provided for evaluating the ability of a protein to function as a transcriptional regulator and as a modulator of plasmid replication, comprising the steps of: (a) independently assaying expression of a first reporter gene and a second reporter gene in a first host cell transformed or transfected with a dual reporter plasmid, wherein the dual reporter plasmid comprises: (i) the first reporter gene operably linked to a binding site for a transcriptional regulator such that transcription of the first reporter gene is modulated by the transcriptional regulator; (ii) the second reporter gene operably linked to a promoter such that transcription of the second reporter gene is not substantially modulated by the transcriptional regulator; and (iii) an origin of replication that comprises a binding site for a modulator of replication; and wherein the first host cell expresses a protein that is a candidate transcriptional regulator and a candidate modulator of plasmid replication; and (b) comparing the levels of expression of the first and second reporter genes determined in step (a) with predetermined levels of expression of the first and second reporter genes in a second host cell, wherein the second host cell is transformed or transfected with the dual reporter plasmid but does not detectably express the candidate protein, and therefrom evaluating the ability of the protein to function as a transcriptional regulator and as a modulator of plasmid replication.

Within other aspects, the present invention provides methods for evaluating a candidate transcriptional regulator and a candidate modulator of plasmid replication, comprising the steps of: (a) independently assaying expression of a first reporter gene and a second reporter gene in a first host cell transformed or transfected a with a dual reporter plasmid, wherein the dual reporter plasmid comprises: (i) the first reporter gene operably linked to a binding site for a transcriptional regulator such that transcription of the first reporter gene is modulated by the transcriptional regulator; (ii) the second reporter gene operably linked to a promoter such that transcription of the second reporter gene is not substantially modulated by the transcriptional regulator; and (iii) an origin of replication that comprises a binding site for a modulator of plasmid replication; and wherein the first host cell expresses both a candidate transcriptional regulator and a candidate modulator of plasmid replication; and (b) comparing the level of expression of the first and second reporter genes determined in step (a) with predetermined levels of expression of the first and second reporter genes in a second host cell transformed or transfected with the dual reporter plasmid but that does not detectably express the candidate transcriptional regulator and the candidate modulator of plasmid replication, and therefrom evaluating an activity of the transcriptional regulator and an activity of the candidate modulator of plasmid replication.

The present invention further provides, within other aspects, methods for screening for an agent that modulates gene expression and/or replication, comprising: (a) contacting a first host cell with a candidate agent, wherein the first host cell is transformed or transfected with a dual reporter plasmid, and wherein the dual reporter plasmid comprises: (i) the first reporter gene operably linked to a binding site for a transcriptional regulator such that transcription of the first reporter gene is modulated by the transcriptional regulator; (ii) a second reporter gene operably linked to a promoter such that transcription of the second reporter gene is not substantially modulated by the transcriptional regulator; and (iii) an origin of replication that comprises a binding site for a modulator of plasmid replication; and wherein the first host cell expresses a protein that is a transcriptional regulator and a modulator of plasmid replication; (b) independently assaying expression of the first and second reporter genes and (c) comparing the level of expression of the first and second reporter genes determined in step (b) with predetermined levels of expression of the first and second reporter genes in a second host cell that is not contacted with a candidate agent, wherein the second host cell is transformed or transfected with the dual reporter plasmid and expresses the protein that is a transcriptional regulator and a modulator of plasmid replication, and therefrom evaluating the ability of the candidate agent to modulate gene expression and plasmid replication.

Within further aspects, the present invention provides methods for screening for an agent that modulates gene expression and/or replication, comprising: (a) contacting a first host cell with a candidate agent, wherein the first host cell is transformed or transfected with a dual reporter plasmid, and wherein the dual reporter plasmid comprises; (i) the first reporter gene operably linked to a binding site for a transcriptional regulator such that transcription of the first reporter gene is modulated by the transcriptional regulator; (ii) a second reporter gene operably linked to a promoter such that transcription of the second reporter gene is not substantially modulated by the transcriptional regulator; and (iii) an origin of replication that comprises a binding site for a modulator of plasmid replication; and wherein the first host cell expresses both a transcriptional regulator and a modulator of plasmid replication; (b) independently assaying expression of the first and second reporter genes; and (c) comparing the level of expression of the first and second reporter genes determined in step (b) with predetermined levels of expression of the first and second reporter genes in a second host cell that is not contacted with a candidate agent, wherein the second host cell is transformed or transfected with the dual reporter plasmid and expresses the transcriptional regulator and the modulator of plasmid replication, and therefrom evaluating the ability of the candidate agent to modulate gene expression and plasmid replication.

The present invention further provides dual reporter plasmids comprising: (a) a first reporter gene operably linked to a binding site for a transcriptional regulator such that transcription of the first reporter gene is modulated by the transcriptional regulator; (b) a second reporter gene that is operably linked to a promoter such that transcription of the second reporter gene is not substantially modulated by the transcriptional regulator; and (c) an origin of replication that comprises a binding site for a modulator of plasmid replication. Within such plasmids, the transcriptional regulator may be a human papillomavirus E2 protein and the protein that stimulates plasmid replication may be a human papillomavirus E1 protein. Within certain embodiments, the levels of expression of the first and second reporter genes may be evaluated concurrently by a calorimetric, fluorometric and/or luminometric assay. For example, the first and second reporter genes may be firefly luciferase or Renilla luciferase.

Within further aspects, the present invention provides dual reporter plasmids, comprising: a) a first reporter gene operably linked to a binding site for a papillomavirus E1 and/or E2 protein such that transcription of the first reporter gene is modulated by the papillomavirus E1 and/or E2 protein; (b) a second reporter gene that is operably linked to a promoter such that transcription of the second reporter gene is not substantially modulated by a papillomavirus E1 and/or E2 protein; and (c) an origin of replication that is bound by a papillomavirus E1 protein.

The present invention further provides host cells transformed or transfected with a dual reporter plasmid as described above. Within certain embodiments the host cell is selected from the group consisting of keratinocytes and C33-A cells.

Within further aspects, the present invention provides methods for screening for an agent that modulates human papillomavirus gene expression and/or replication, comprising: (a) contacting a candidate agent with a host cell transformed or transfected with a dual reporter plasmid as described above, wherein the host cell expresses human papillomavirus proteins E1 and E2; (b) independently assaying expression of the first and second reporter gene; and (c) comparing the level of expression of the first and second reporter genes determined in step (b) with predetermined levels of expression of the first and second reporter genes in a second host cell that is not contacted with a candidate agent, wherein the second host cell is transformed or transfected with the dual reporter plasmid and expresses human papillomavirus proteins E1 and E2, and therefrom evaluating the ability of the candidate agent to modulate gene expression and plasmid replication.

The present invention further provides kits for evaluating an effect of an agent on gene expression and/or plasmid replication, comprising: (a) a cell line, wherein the cell line is transformed or transfected with a dual reporter plasmid as described above; and (b) a supply of reagents for detecting expression of the first and second reporter genes.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIGS. 4A and 4B are three dimensional graphs illustrating the level of firefly (4A) and Renilla (4B) luciferase activity generated using C 33-A cells transfected with a representative dual reporter plasmid. The dual reporter plasmid contained (a) the coding region for firefly luciferase immediately downstream of the SV40 promoter linked to four E2 binding sites and (b) the coding region for Renilla luciferase on the other side of the plasmid and downstream of an HSV thymidine kinase promoter. Cells were also transfected with varying amounts of an expression plasmid for the HPV-6b E1 and/or E2 proteins, as indicated. Cells were lysed two days after transfection and firefly and Renilla luciferase activities determined.

In FIGS. 7C and 7D, the experiment was the same except that the cells were incubated in the presence of the replication inhibitor cytosine arabinoside (araC).

DETAILED DESCRIPTION OF THE INVENTION

Figure 1:
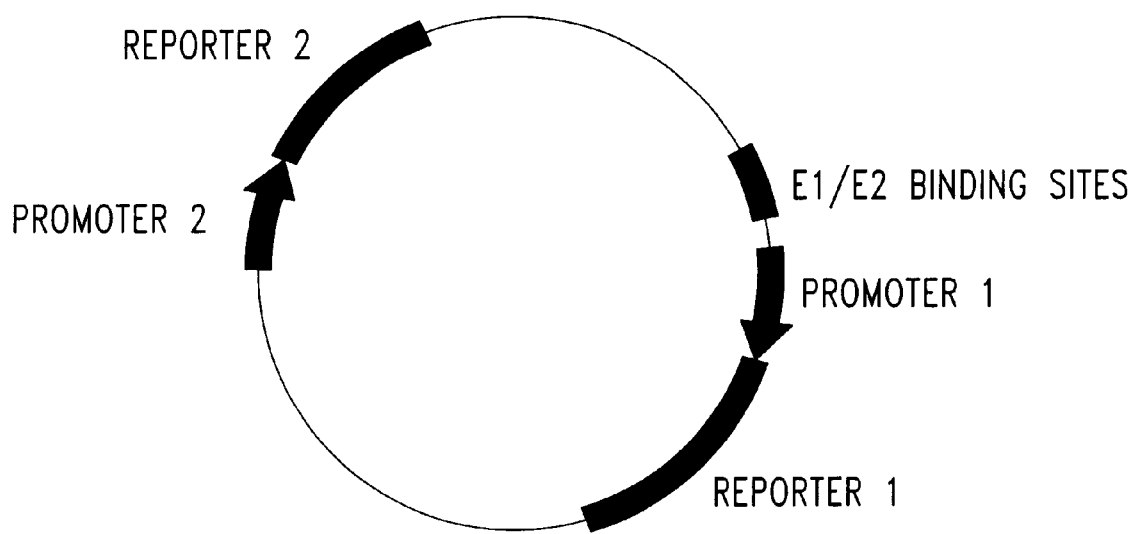
FIG. 1 is a diagram illustrating a representative dual reporter plasmid. Reporter gene 1 is operably linked to a regulatory sequence that is an HPV E1/E2 binding site. Reporter gene 2 is operably linked to a promoter that is not substantially modulated by E1/E2 binding. In the presence of E2, an increase in activity of the protein encoded by reporter gene 1 is observed, and no substantial increase in the activity of the protein encoded by reporter gene 2 is detected. In the presence of E 1 and E2, an increase in activity of proteins encoded by reporter genes 1 and 2 can be detected.

As noted above, the present invention is generally directed to plasmid systems comprising dual reporters for use in the independent evaluation of transcription and replication. Such systems may be used for the study of endogenous factors involved in these processes, or for the screening of agents that modulate one or both processes. Agents identified using certain dual reporter plasmids provided herein may be used, for example, for the treatment or prevention of viral infections. Other plasmids may be used to for the study of cellular factors and to identify agents that modulate cellular processes.

Throughout the present application, a system for the independent evaluation of HPV transcription and replication is described as an example of a dual reporter plasmid system. It will be apparent to those of ordinary skill in the art that the dual reporter concept may be applied to the study of other pathogens for which it is desirable to perform independent evaluations of transcription and replication. In particular, such systems may be readily applied to evaluate transcription and replication within viruses such as SV40, polyomavirus, cytomegalovirus, herpes viruses and the like. Accordingly, the HPV dual reporter system provided herein is merely exemplary. and is not intended to limit the scope of the present invention.

A "dual reporter plasmid," as used herein, is a plasmid that comprises two separately-regulated reporter genes, such that transcription of the first and second reporter genes may be assayed independently. The first reporter gene is operably linked to a promoter and a regulatory sequence such that transcription of the reporter gene may be modulated (inhibited or enhanced) by a transcriptional regulator. A regulatory sequence may be any DNA sequence that is bound by a transcriptional regulator. preferably the regulatory sequence ranges from 4 to 16 nucleotides in length. Regulatory sequences may generally be identified using well known promoter assays A regulatory sequence is "operably linked" to the first reporter gene if it is positioned such that the binding of the transcriptional regulator to the regulatory sequence results in a statistically significant change in the level of transcription. The regulatory sequence should further be positioned such that transcription of the second reporter gene is not substantially modulated by the transcriptional regulator (i.e., any effect on transcription of the second reporter gene should be less than 50% of the effect on the first reporter gene). Preferably, the regulatory sequence is located within 100 bp of the first reporter gene, and at least 2 kb, and more preferably 3 kb, away from the second reporter gene. Sequences that insulate enhancer effects may, but need not, be positioned between the regulatory sequence and the second reporter gene.

A "transcriptional regulator" is any compound that is capable of binding (directly or by way of other molecules) to the regulatory sequence and causing a change in the level of transcription of an operably linked gene. The term "binding," as used herein, refers to a noncovalent association between two separate molecules such that a "complex" is formed. The ability to bind may be evaluated using standard techniques, such as affinity assays (e.g., affinity chromatography or electrophoretic mobility shift assay) or using footprinting techniques known in the art. In general, an interaction between a transcriptional regulator and a regulatory sequence that can be detected at a level that is statistically above background within such an assay is considered "binding." Alternatively, for transcriptional regulators that bind directly to a regulatory sequence, a binding constant for the formation of the complex may be determined. The binding constant is the value obtained when the concentration of the complex is divided by the product of the component concentrations. In general, two compounds are said to "bind," in the context of the present invention, when the binding constant for complex formation at physiological conditions exceeds about $10^4$ L/mol, preferably the binding constant exceeds about $10^6$ L/mol and more preferably the binding constant exceeds about $10^8$ L/mol. The binding constant may be determined using methods well known in the art. For transcriptional regulators that bind indirectly (i.e., by way of one or more other proteins), each protein-protein interaction should satisfy the above criteria for binding.

The ability of a transcriptional regulator to cause a change in the level of transcription of an operably linked gene may be assessed using standard promoter assays, which are well known in the art. In general, a transcriptional regulator should result in a statistically significant change in transcription of a linked gene, and preferably the change is at least two fold. Transcriptional regulators may include endogenous cellular proteins and other factors, viral proteins and exogenous compounds. Many such regulators, and their corresponding regulatory sequences, are known in the art. For example, a transcriptional regulator may be a papillomavirus E1 or E2 protein. Within other embodiments, a transcriptional regulator may be a polyomavirus or SV40 T antigen.

The second reporter gene present within a dual reporter plasmid is designed to permit an evaluation of plasmid replication within a host cell. The second reporter gene is operably linked to a promoter such that transcription is not substantially modulated by the transcriptional regulator of interest. To minimize an effect of the transcriptional regulator on the second reporter gene, the first and second reporter genes should ideally be as far apart on the plasmid as possible. Head-to-head orientations, with the regulatory sequence flanked by the two reporter genes on either side are to be avoided. Suitable promoters for use with the second reporter gene include, but are not limited to, HSV thymidine kinase promoters, CMV MIEP, SV40 early promoter and retroviral LTRs. The level of expression of protein encoded by the second reporter gene in a cell transfected by such a plasmid is generally indicative of the level of plasmid replication.

It should be noted that certain regulatory sequences may operate at a distance, and thus may affect transcription of the second reporter gene. Any such effect should be lower than the effect on the transcription of the first reporter gene, to which the regulatory sequence is operably linked. To determine whether the binding of a transcriptional regulator to a regulatory sequence alters the transcription of the second reporter gene, standard plasmid digests may be employed to assess the effect on plasmid replication. If there is a detectable effect on transcription, a change in expression of the second reporter gene may be due to a combination of effects on transcription and replication. However, the effect on transcription may then be subtracted from the change in expression level, permitting an accurate evaluation of plasmid replication based on expression of the second reporter gene. Within a dual reporter system, as noted above, the transcriptional regulator should not "substantially modulate" transcription of the second reporter gene. In other words, the effect of the transcriptional regulator on the second reporter gene should be less than 50% of the effect on the first reporter gene, preferably less than 60%, and more preferably less than 67%.

A dual reporter plasmid further comprises an origin of replication that permits replication in a desired host cell. A minimum origin of replication contains sufficient sequence to confer appropriate replication patterns on a heterologous polynucleotide (e.g., a plasmid). Origins of replication for use within the dual reporter plasmids provided herein permit maintenance of the plasmid in a host cell and permit modulation of plasmid replication by a protein modulator of replication. Such an origin of replication comprises a binding site for a modulator of plasmid replication. Binding of a modulator of plasmid replication (either directly or indirectly, as described above) to the binding site results in a detectable change in plasmid replication, and a corresponding detectable change in the level of the first and second reporter proteins. In general, the change in the level of the second reporter protein is indicative of the effect of the modulator on plasmid replication. Origins of replication for use within the present invention may generally be identified by evaluating the ability of a candidate origin of replication to confer the ability to replicate on heterologous sequences, using techniques that are well known in the art.

Figure 2:
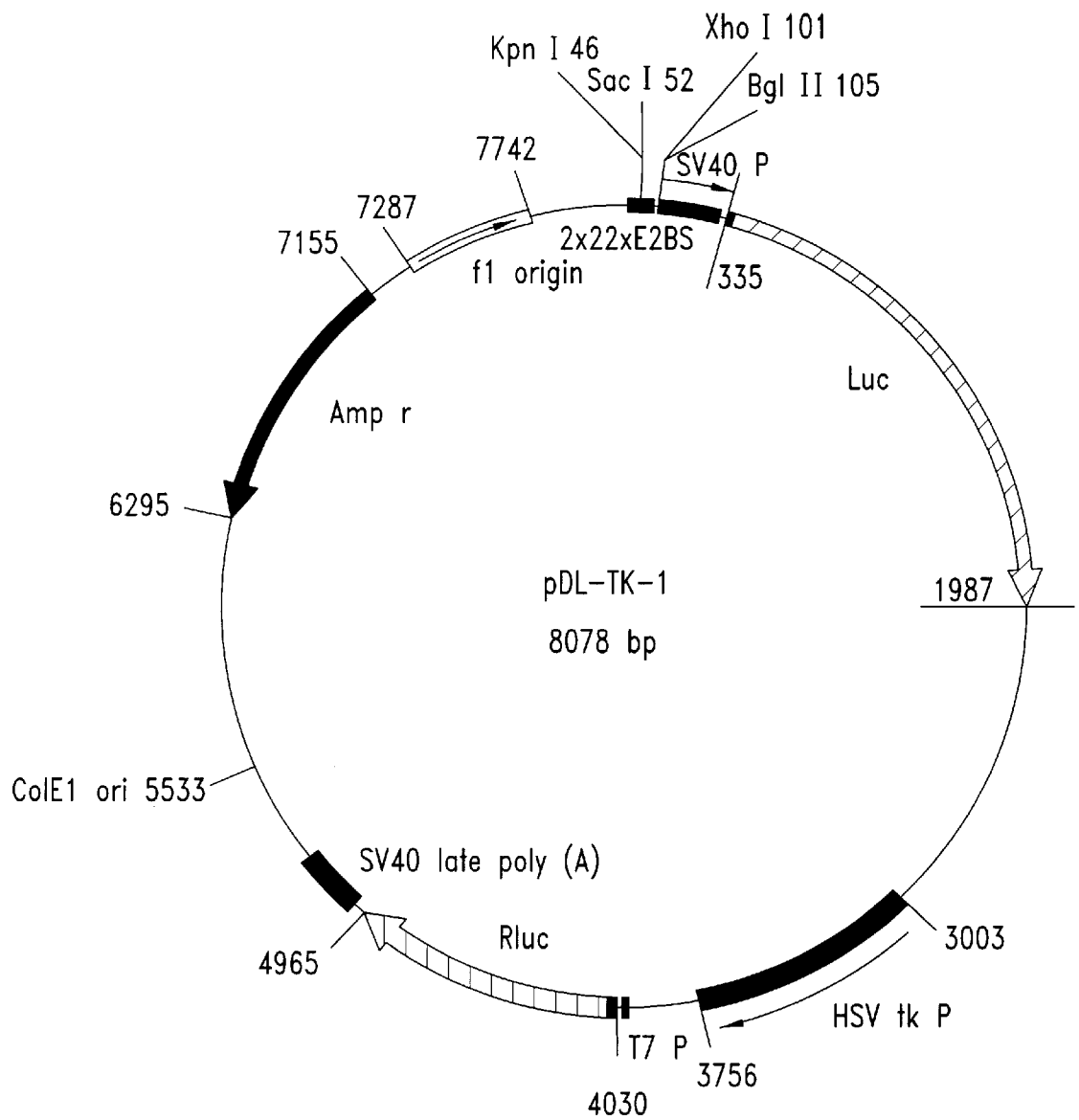
FIG. 2 is a plasmid map illustrating a representative dual reporter plasmid.

Regulatory sequences and origins of replication are generally selected to facilitate the study of transcription and replication or to permit screens for compounds that modulate transcription and/or replication within a particular system (e.g., viral). Many such sequences are known in the art, and others may be identified using standard techniques, such as binding assays and functional assays employing truncated or modified nucleic acid sequences to identify minimal functional units. Within one preferred embodiment, a dual reporter plasmid may be designed for evaluating papillomavirus (e.g., human papillomavirus) proteins and other factors for the ability to modulate transcription and replication of a papillomavirus genome. Within such an embodiment, the transcriptional regulator may be human papillomavirus (HPV) E2 protein or E1 protein. One regulatory sequence to which E2 is known to bind is $ACCN_6GGT$ (SEQ ID NO:1), wherein $N_6$ indicates a series of six independently selected nucleotides. A preferred regulatory sequence for E2 binding is ACCGAAAACGGT (SEQ ID NO:2). The modulator of HPV genome replication may be HPV E1 protein. One origin of replication sufficient to permit modulation of HPV plasmid replication contains multimers of the E2 binding site recited above (see Kovelman et al., *J. Virol.* 70:7549–7560, 1996). A representative dual reporter plasmid comprising HPV elements is depicted in FIG. 1, and a more detailed plasmid map is shown in FIG. 2.

The precise reporter genes used within a dual reporter plasmid are not critical, provided that the first and second reporter genes are different and permit independent assay of the expression of the first and second reporter genes. In general, any gene whose level of expression can be conveniently detected may be used as a reporter gene. Expression of a reporter gene may be determined at the transcriptional level (i.e., using any of a variety of well known hybridization or amplification techniques to assess the level of mRNA transcribed from the reporter gene), at the translational level (i.e., using a compound, such as an antibody, that binds to the protein encoded by the reporter gene to assess the level of such protein synthesized in any standard assay format, such as ELISA) or at the level of activity (i.e., using an assay to measure an activity (e.g., enzymatic) of a protein encoded by the reporter gene. Preferably, reporter gene expression is determined by measuring an activity of the encoded protein. Suitable reporter genes include, but are not limited to, luciferase (e.g., firefly or Renilla), green fluorescent protein, β-galactosidase and chloramphenicol acetyl transferase. Within one embodiment the first and second reporter genes are different forms of luciferase.

Optionally, a dual reporter plasmid may comprise any of a variety of additional components, such as a selectable marker or a polynucleotide encoding one or more transcriptional regulators and/or modulators of replication.

In general, any cell that expresses or can be supplemented with factors necessary for transcription of the first reporter gene and replication of the dual reporter plasmid may be used as a host cell. For example, cells that support viral propagation may be used as host cells for dual reporter plasmids containing a viral regulatory sequence and origin of replication. For a dual reporter plasmid comprising a regulatory sequence that is an HPV E1 and/or E2 binding site, and an HPV origin of replication, suitable host cells include, but are not limited to, C33-A (a cell line derived from a cervical carcinoma) or normal epidermal keratinocytes. C33-A cells (ATCC, Manassas, Va.) do not contain integrated papillomavirus DNA, which makes these cells superior to HeLa cells for papillomavirus studies. It will be apparent that a host cell need not, in its native state, express all factors needed for transcription and replication of the plasmid, provided that the host cell may be genetically modified to express necessary factors and/or may be supplemented by culture in the presence of such factors. Suitable host cells may be transformed or transfected with a dual reporter plasmid using standard techniques known in the art to be appropriate for the particular cell type. Host cells transformed or transfected with a dual reporter plasmid may be maintained as a cell line (in which the dual reporter plasmid is maintained episomally), for use within the assays provided herein. Such host cells and cell lines are specifically contemplated by the present invention.

Following transfection and incubation to permit transcription of the reporter genes and replication of the plasmid, reporter gene activity may be assessed using a technique appropriate for the particular reporter protein. In many cases, a reporter protein is an enzyme capable of detection by routine calorimetric, fluorometric or luminometric techniques. Assays appropriate for particular reporter genes are well known in the art. For example, luciferase activity may be detected using standard luminometric methods, with luciferin as the enzyme substrate (de-Wet et al. *Mol. Cell. Biol.* 7:725–737, 1987). Appropriate methods for detecting the level of expression of other reporter genes will be apparent to those of ordinary skill in the art and may be found, for example, in Sambrook et al., *Molecular Cloning: A Laboratory Manual*, Cold Spring Harbor Laboratories, Cold Spring Harbor, N.Y., 1989 and in manufacturer's protocols. Assays for both reporter genes may be performed concurrently, or may be performed on separate aliquots either simultaneously or sequentially.

In general, a signal detected in a reporter protein assay is compared to a signal that is detected in the absence of one or more factors whose activity as transcriptional regulators and modulators of replication is to be assessed. Alternatively, the relevant comparison may be to the signal detected in the presence of a different factor, or a variant of the factor. In general, a change is signal is considered significant if it satisfies the requirements for statistical significance known in the art. Preferably, the signal differs by at least 10%, and preferably by at least 50%, due to the presence of the transcriptional regulator or modulator of replication.

Dual reporter plasmids as provided herein have significant advantages over other approaches to evaluating transcription and replication. In particular, screens for reporter gene activity are rapid and can be performed in a high throughput fashion. In addition, both processes occur on the same molecule, which more accurately reflects the natural environment.

As noted above, a dual reporter plasmid may be used experimentally for the study of endogenous factors involved in transcription and replication (e.g., viral), or for the screening of agents that modulate one or both processes. For example, a host cell may be transformed or transfected with a dual reporter plasmid and with one or more plasmids comprising polynucleotide(s) that encode one or more proteins whose activity as transcriptional regulators and modulators of replication is to be assessed. Such polynucleotide(s) may be operably linked to an inducible promoter (i.e., a promoter that is modulated by an externally controlled factor, such as promoters regulated by steroid hormones (mammalian or others, such as ecdysone and analogues functioning on a heterologous insect cell receptor) or other compounds such as tetracycline, in conjunction with the bacterial tet repressor. A single protein that may function as a transcriptional regulator and as a modulator of replication may be used, or two different proteins may be employed. For example, host cells may be genetically modified to express HPV E1 and/or E2 (or variants of such proteins) and may be transformed or transfected with a dual reporter plasmid as shown in FIG. 1. By inducing expression of one or both proteins, and subsequently evaluating the level of first and second reporter gene activity, the effect of such proteins on transcription and HPV replication may be assessed. In particular, the levels of expression of the first and second reporter genes determined in the presence of the protein being studies may be compared with predetermined levels of expression of the first and second reporter genes in a similar host cell that comprises the dual reporter plasmid but does not detectably express the candidate protein(s). When the activities of multiple proteins are assayed, reporter gene expression is preferably evaluated in a similar host cell that does not detectably express any of the candidate proteins, as well as in a cell that expresses only one candidate protein. Changes in reporter gene expression that are statistically significant indicate that the protein modulates transcription and/or translation.

To screen agents for the ability to modulate transcription and/or replication, a host cell that comprises a dual reporter plasmid, and that expresses any necessary transcriptional regulator(s) and modulator(s) of plasmid replication, is contacted with a candidate agent. Contact may be achieved by incubation with the candidate agent or by transfection of the host cell with a polynucleotide that encodes the candidate agent under conditions that permit expression of the candidate within the host cell. Regardless of the precise method used, the host cell and the candidate agent are contacted for a period of time and under conditions sufficient to permit the candidate agent to interact with cellular components. In general, host cells may be incubated with exogenous candidate agents for 1–24 hours. For candidate agents that are expressed recombinantly within the host cell, incubation of the host cell for 24 to 72 hours following induction of candidate agent expression, is generally sufficient. It will be apparent to those of ordinary skill in the art that contact times may vary with the specific host cell/dual reporter plasmid combination, and optimal contact times may be readily determined. Following contact, the level of transcription of the first and second reporter genes is determined as described above, and is compared to predetermined levels of transcription in a similar host cell that is not contacted with the candidate agent. An agent has the ability to modulate replication if contact with the agent results in a statistically significant change in the activity of the second reporter gene, and has the ability to modulate transcription if contact with the agent results in a statistically significant change in activity of the first reporter gene, relative to the activities observed in the absence of the agent.

To screen compounds for the ability to modulate HPV transcription and/or replication, a host cell that comprises a dual reporter plasmid as depicted in FIG. 1, and that expresses HPV E1 and E2 (or variants thereof), is contacted with a candidate modulator. Within certain embodiments, the cell expresses E1 and E2 due to transfection with plasmid(s) comprising genes encoding these proteins operably linked to a promoter, such that E1 and E2 are expressed within the transfected cell. Contact and the subsequent assays, may generally be achieved as described above.

The present invention further provides kits for use in evaluating the effect of an agent on gene expression and/or plasmid replication. Such kits typically comprise two or more components necessary for performing the assay. Such components may be compounds, reagents and/or containers or equipment. For example, one container within a kit may contain a host cell line transformed or transfected with a dual reporter plasmid as provided herein. One or more additional containers may enclose elements, such as reagents or buffers, to be used in an assay to detect expression of a reporter gene or the level of plasmid replication. Alternatively, a kit may comprise a dual reporter plasmid and one or more different plasmids capable of expressing one or more transcriptional regulators and/or modulators of replication.

Compounds identified using such screens may have utility as therapeutic agents. For example, modulators that inhibit HPV gene expression and/or replication. or polynucleotides encoding such modulators, may be used as antiviral agents. In particular, such modulators may find use in the treatment of HPV-associated conditions such as condylomata acuminatum (genital warts) and cervical cancer. For such applications, modulating agents or polypeptides encoding such agents may be present within a pharmaceutical composition comprising one or more pharmaceutically or physiologically acceptable carriers, diluents or excipients. To prepare a pharmaceutical composition, an effective amount of one or more polynucleotides and/or modulating agents is mixed with a suitable pharmaceutical carrier. Solutions or suspensions used for parenteral, intradermal, subcutaneous or topical application can include, for example, a sterile diluent (such as water), saline solution, fixed oil, polyethylene glycol, glycerin, propylene glycol or other synthetic solvent; antimicrobial agents (such as benzyl alcohol and methyl parabens); antioxidants (such as ascorbic acid and sodium bisulfite) and chelating agents (such as ethylenediaminetetraacetic acid (EDTA));

buffers (such as acetates, citrates and phosphates). If administered intravenously, suitable carriers include physiological saline or phosphate buffered saline (PBS), and solutions containing thickening and solubilizing agents, such as glucose, polyethylene glycol, polypropylene glycol and mixtures thereof. In addition, other pharmaceutically active ingredients and/or suitable excipients such as salts, buffers and stabilizers may, but need not, be present within the composition.

A pharmaceutical composition is generally formulated and administered to exert a therapeutically useful effect while minimizing undesirable side effects. The number and degree of acceptable side effects depend upon the condition for which the composition is administered. For example, certain toxic and undesirable side effects that are tolerated when treating life-threatening illnesses, such as tumors, would not be tolerated when treating disorders of lesser consequence. The concentration of active component in the composition will depend on absorption, inactivation and excretion rates thereof, the dosage schedule and the amount administered, as well as other factors that may be readily determined by those of skill in the art.

A pharmaceutical composition may be prepared with carriers that protect the active component against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art. Such formulations may generally be prepared using well known technology and administered by, for example, oral, rectal or subcutaneous implantation, or by implantation at the desired target site. Sustained-release formulations may contain a polynucleotide or modulating agent dispersed in a carrier matrix and/or contained within a reservoir surrounded by a rate controlling membrane. Preferably the formulation provides a relatively constant level of modulating agent release. The amount of active component contained within a sustained release formulation depends upon the site of implantation, the rate and expected duration of release and the nature of the condition to be treated or prevented.

Pharmaceutical compositions of the present invention may be administered in a manner appropriate to the disease to be treated (or prevented). Administration may be effected by incubation of cells ex vivo or in vivo, such as by topical treatment, delivery by specific carrier or by vascular supply. Appropriate dosages and a suitable duration and frequency of administration will be determined by such factors as the condition of the patient, the type and severity of the patient's disease and the method of administration. In general, an appropriate dosage and treatment regimen provides a modulator in an amount sufficient to provide therapeutic and/or prophylactic benefit (i.e., an amount that ameliorates the symptoms or treats or delays or prevents progression of the condition). The precise dosage and duration of treatment is a function of the disease being treated and may be determined empirically using known testing protocols or by testing the compositions in model systems known in the art and extrapolating therefrom. Dosages may also vary with the severity of the condition to be alleviated. The composition may be administered one time, or may be divided into a number of smaller doses to be administered at intervals of time. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art, and for any particular subject, specific dosage regimens may be adjusted over time according to the individual need.

For pharmaceutical compositions comprising polynucleotides, the polynucleotide may be present within any of a variety of delivery systems known to those of ordinary skill in the art, including nucleic acid, bacterial and viral expression systems, and colloidal dispersion systems such as liposomes. Appropriate nucleic acid expression systems contain the necessary DNA sequences for expression in the patient (such as a suitable promoter and terminating signal, as described above). The DNA may also be "naked," as described, for example, in Ulmer et al., *Science* 259:1745–1749, 1993.

Various viral vectors that can be used to introduce a nucleic acid sequence into the targeted patient's cells include, but are not limited to, vaccinia or other pox virus, herpes virus, retrovirus, or adenovirus. Techniques for incorporating DNA into such vectors are well known to those of ordinary skill in the art. Preferably, the retroviral vector is a derivative of a murine or avian retrovirus including, but not limited to, Moloney murine leukemia virus (MoMuLV), Harvey murine sarcoma virus (HaMuSV), murine mammary tumor virus (MuMTV), and Rous Sarcoma Virus (RSV). A retroviral vector may additionally transfer or incorporate a gene for a selectable marker (to aid in the identification or selection of transduced cells) and/or a gene that encodes the ligand for a receptor on a specific target cell (to render the vector target specific).

Viral vectors are typically non-pathogenic (defective), replication competent viruses, which require assistance in order to produce infectious vector particles. This assistance can be provided, for example, by using helper cell lines that contain plasmids that encode all of the structural genes of the retrovirus under the control of regulatory sequences within the LTR, but that are missing a nucleotide sequence which enables the packaging mechanism to recognize an RNA transcript for encapsulation. Such helper cell lines include (but are not limited to) Ψ2, PA317 and PA12. A retroviral vector introduced into such cells can be packaged and vector virion produced. The vector virions produced by this method can then be used to infect a tissue cell line, such as NIH 3T3 cells, to produce large quantities of chimeric retroviral virions.

Another targeted delivery system for polynucleotides is a colloidal dispersion system. Colloidal dispersion systems include macromolecule complexes nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). RNA, DNA and intact virions can be encapsulated within the aqueous interior and delivered to cells in a biologically active form. The preparation and use of liposomes is well known to those of ordinary skill in the art.

The following Examples are offered by way of illustration and not by way of limitation.

EXAMPLES

Example 1

Preparation of HPV Dual Reporter Plasmid

This Example illustrates the preparation of a plasmid system for the independent evaluation of HPV transcription and translation.

A. Plasmid Construction

Dual reporter plasmid pDL-TK1 was prepared to contain (a) the coding region for firefly luciferase immediately downstream of an SV40 promoter linked to four E2 binding sites and (b) the coding region for Renilla luciferase on the other side of the plasmid and downstream of an HSV thymidine kinase promoter. The plasmid was constructed from a BamHI fragment of p2×2×E2BS-luc (a derivative of pGL2-Promoter (Promega, Madison, Wis.) containing HPV-6b E2 binding sites) and BamHI-BglII fragment from PRL-TK (Promega, Madison, Wis.). The plasmid has a size of 8078 base pairs. Positions 7–93 have the following sequence (containing four underlined E2 binding sites):

ACCGAAAACGGTTCAACCGAAAACGGTCCCGGGAGGTA
CCGAGCTCTTACGCGTGCTAGCACCGAAAACGGTTCAAC
CGAAAACGGT (SEQ ID NO:3)

Downstream of the SV40 promoter is the SV40 promoter and a firefly luciferase gene (positions 335–1987). The HSV TK promoter is located at positions 3003–3755, and controls expression of the Renilla luciferase gene (positions 4030–4965). Other plasmid components, including origins of replication and an ampicillin resistance gene are indicated in the plasmid map shown in FIG. 2.

B. Evaluation of Reporter Gene Expression

Normal human keratinocytes were transfected with the dual reporter plasmid described above. Cells were also transfected with varying amounts of expression plasmids for the papillomavirus E1 and/or E2 proteins. Cells were lysed two days after transfection and firefly and Renilla luciferase activities determined using the Dual Luciferase Reporter Assay System (Promega, Madison. Wis.).

Figure 3B:
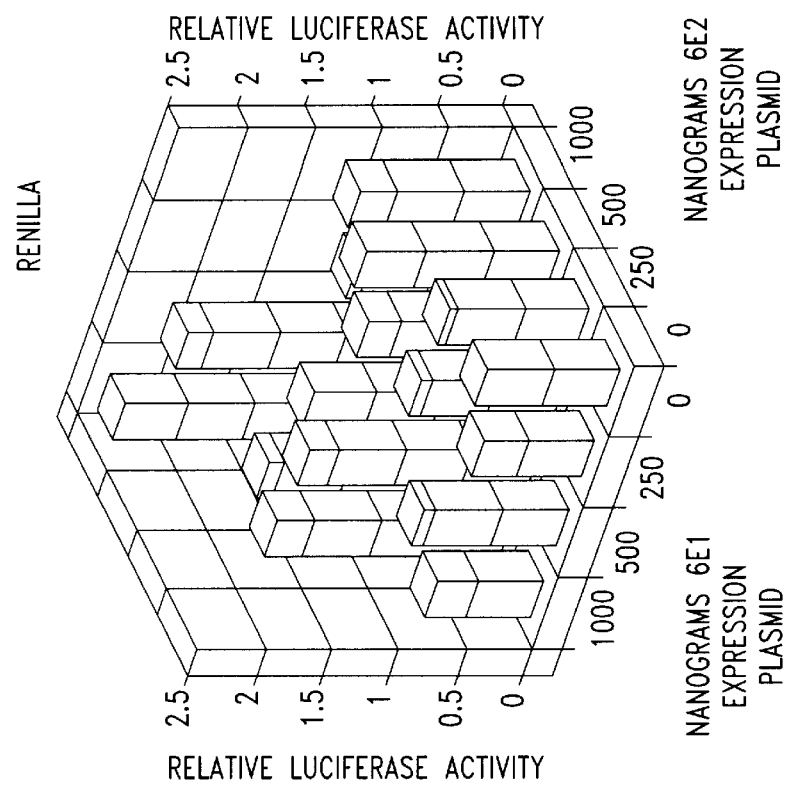
FIGS. 3A and 3B are three dimensional graphs illustrating the level of firefly (3A) and Renilla (3B) luciferase activity generated using normal human keratinocytes transfected with a representative dual reporter plasmid. The dual reporter plasmid contained (a) the coding region for firefly luciferase immediately downstream of the SV40 promoter linked to four E2 binding sites and (b) the coding region for Renilla luciferase on the other side of the plasmid and downstream of an HSV thymidine kinase promoter. Cells were also transfected with varying amounts of an expression plasmid for the human papillomavirus type 6b (HPV-6b) E1 and/or E2 proteins, as indicated. Cells were lysed two days after transfection and firefly and Renilla luciferase activities determined.
Figure 3A:
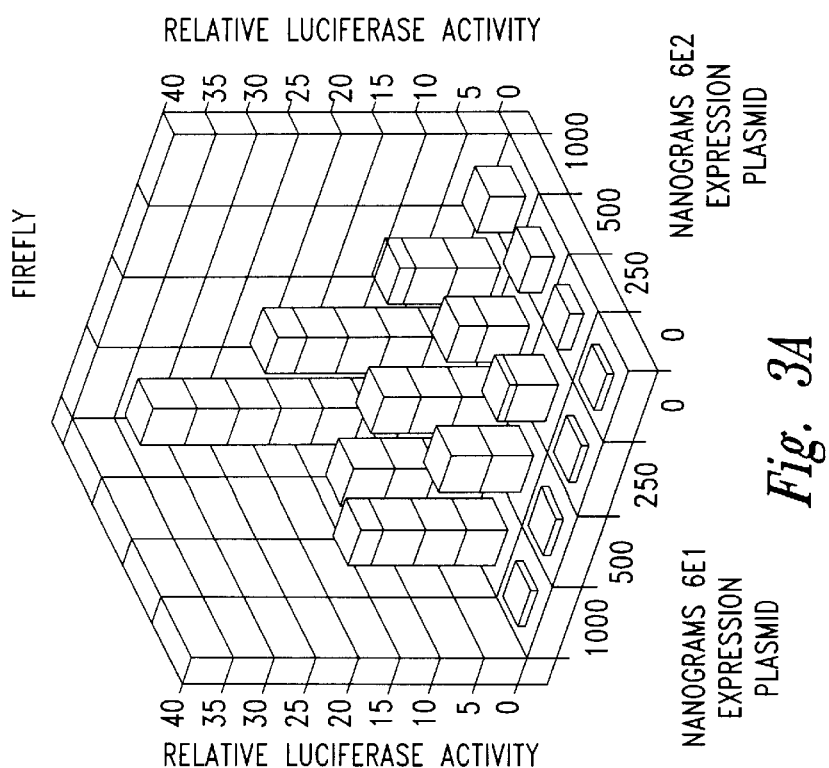

The results are shown in FIGS. 3A and 3B. E2 alone was found to activate the proximal reporter (firefly luciferase) 3–4 fold and did not activate the distal promoter (Renilla luciferase). In the presence of E2, E1 increased activation of firefly luciferase expression up to 35-fold (i.e., 7–10 fold better than with E2 alone), but had at most a 2-fold effect on Renilla luciferase expression. Thus. E1 expression did not increase E2 activation of firefly luciferase expression merely by stimulating replication of the entire plasmid, as that would have resulted in a proportional increase in firefly and Renilla luciferase activities. In this manner, this representative dual-reporter assay system allowed rapid determination of direct effects on transcription and replication.

A similar experiment was performed using C 33-A cells, which are derived from a cervical carcinoma. The results, presented in FIGS. 4A and 4B show a similar pattern of reporter gene activities.

Figure 5B:
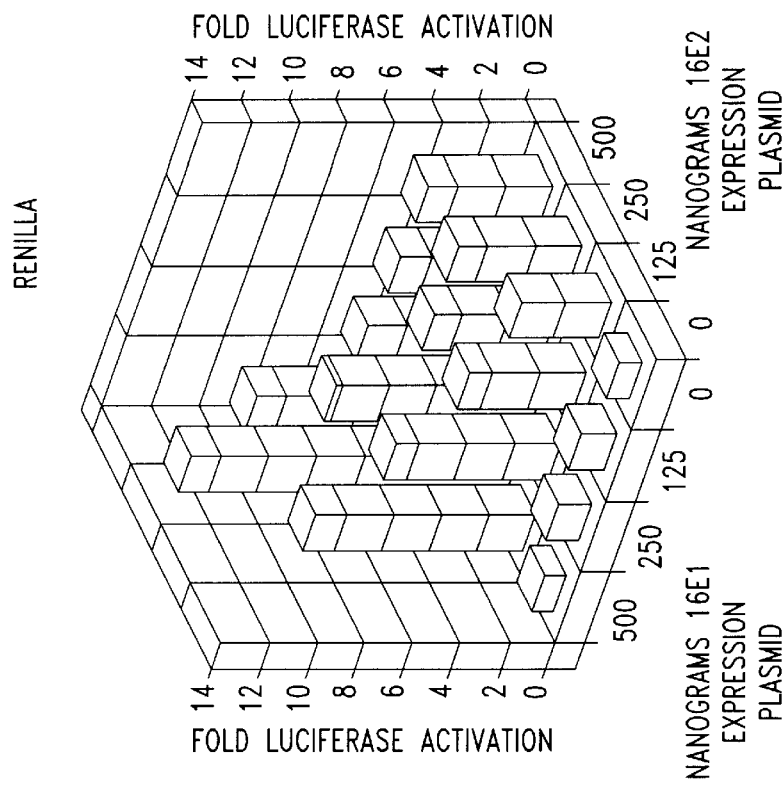
FIGS. 5A and 5B are three dimensional graphs illustrating the level of firefly (5A) and Renilla (5B) luciferase activity generated using C 33-A cells transfected with a representative dual reporter plasmid. The dual reporter plasmid contained (a) the coding region for firefly luciferase immediately downstream of the SV40 promoter linked to four E2 binding sites and (b) the coding region for Renilla luciferase on the other side of the plasmid and downstream of an HSV thymidine kinase promoter. Cells were also transfected with varying amounts of an expression plasmid for the HPV-16 E1 and/or E2 proteins, as indicated. Cells were lysed two days after transfection and firefly and Renilla luciferase activities determined.
Figure 5A:
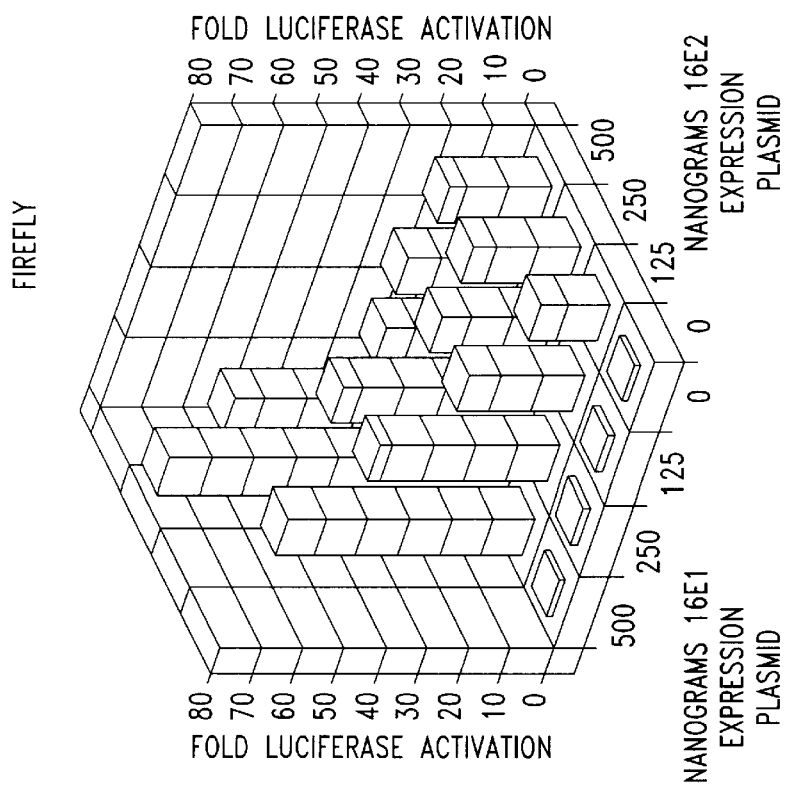

Another experiment was performed as described for FIGS. 4A and 4B, except that the expression plasmid transfected further contained coding regions for the HPV-16 E1 and E2 proteins. The results are shown in FIGS. 5A and 5B. HPV-16 E2 proteins are more active than HPV-6b E2 proteins (see Kovelman et al., *J. Virol.* 70:7549–7560, 1996), and this effect is seen in comparing FIGS. 5A and 5B with FIGS. 4A and 4B. Nonetheless, the same pattern of stimulation of reporter gene activities in the presence of the E1 protein was observed.

Figure 6B:
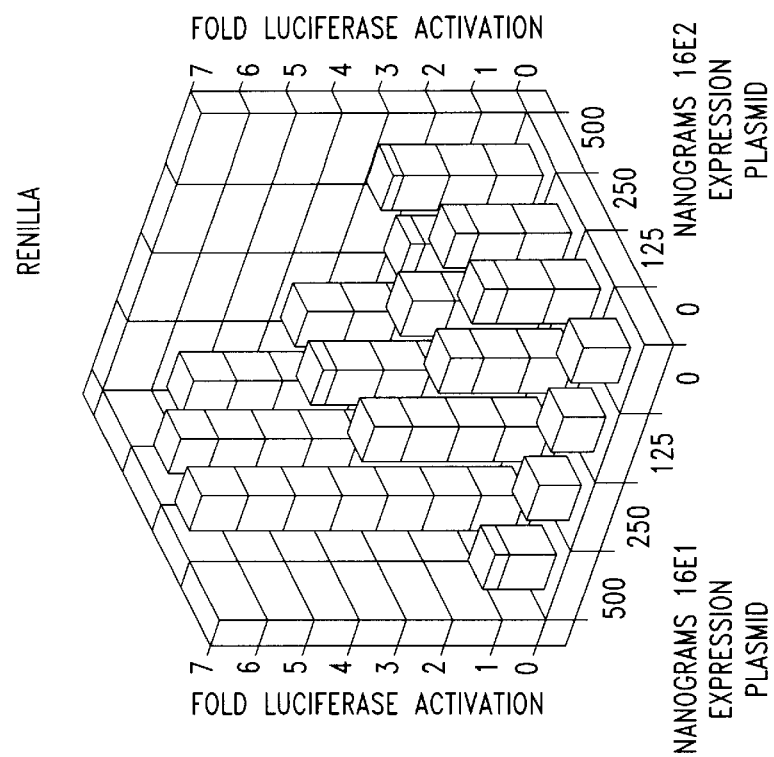
FIGS. 6A and 6B are three dimensional graphs illustrating the level of firefly (5A) and Renilla (5B) luciferase activity generated using C 33-A cells transfected with a representative dual reporter plasmid. The experiment was identical to that shown in FIGS. 5A and 5B, except that the dual reporter plasmid was pDL-TK-2, which is the same as pDL-TK-1 except that the HSV TK promoter -Renilla luciferase cassette was present in the plasmid in the opposite orientation.
Figure 6A:
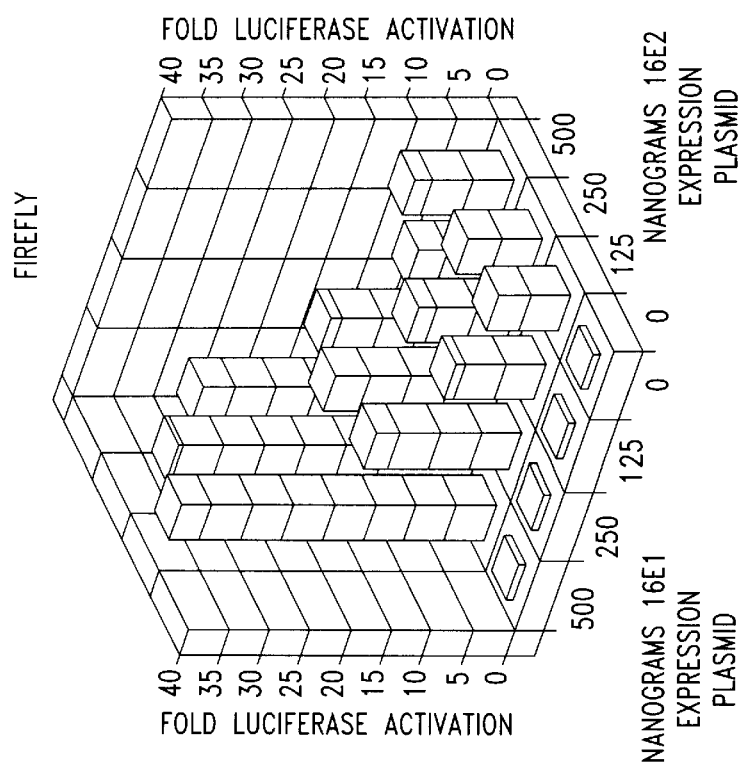

Another experiment was performed as described for FIGS. 5A and 5B, except that the dual reporter plasmid was pDL-TK-2, which is the same as pDL-TK-1 except that the HSV TK promoter-Renilla luciferase cassette was present in the plasmid in the opposite orientation. The results, shown in FIGS. 6A and 6B show the same pattern of stimulation.

Figures 7A, 7B:
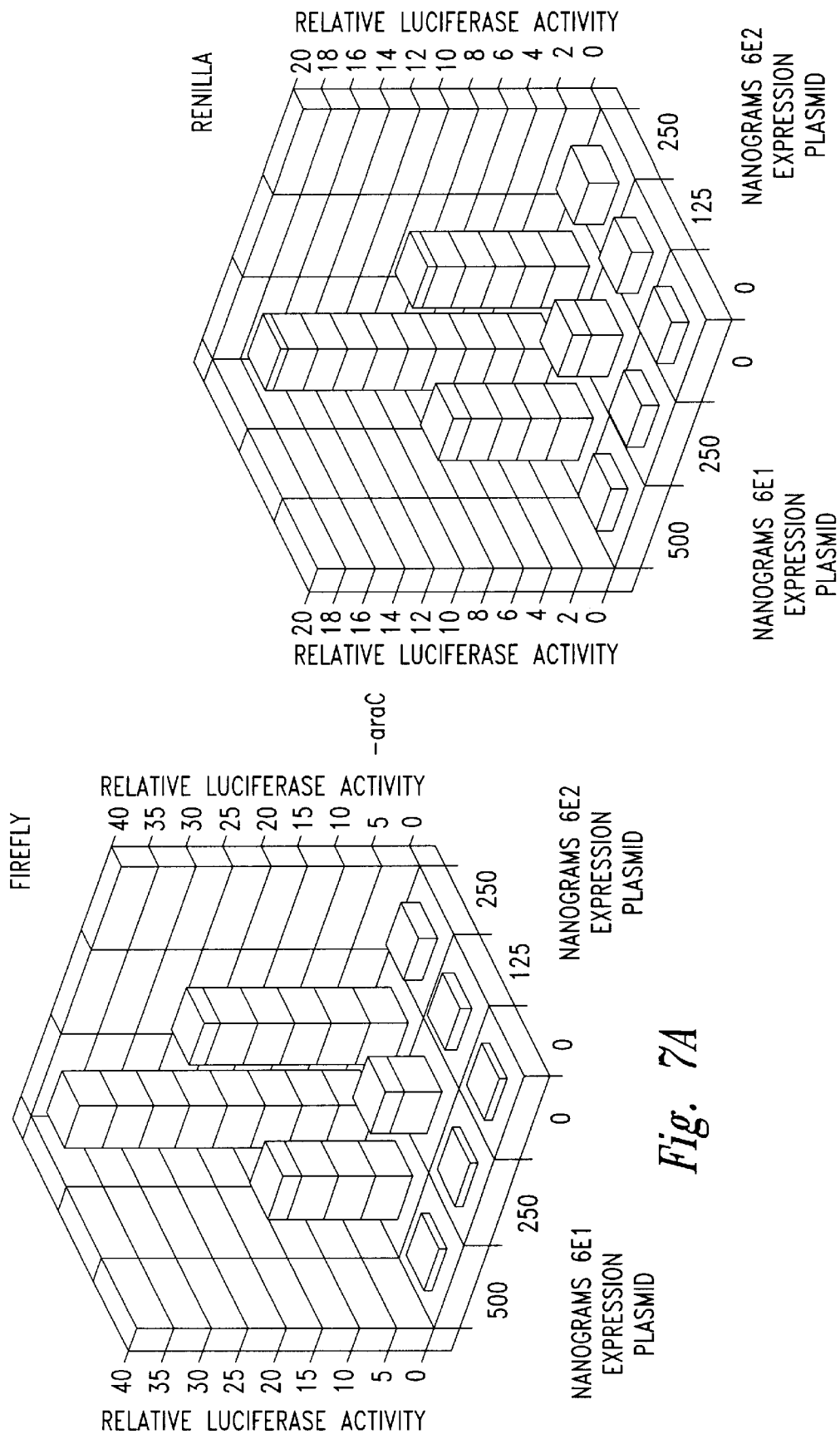
FIGS. 7A–7D are three dimensional graphs illustrating the level of firefly (7A) and Renilla (7B) luciferase activity generated using C 33-A cells transfected with a representative dual reporter plasmid. The results in FIGS. 7A and 7B are shown for an experiment performed as described for FIGS. 4A and 4B.
Figures 7C, 7D:
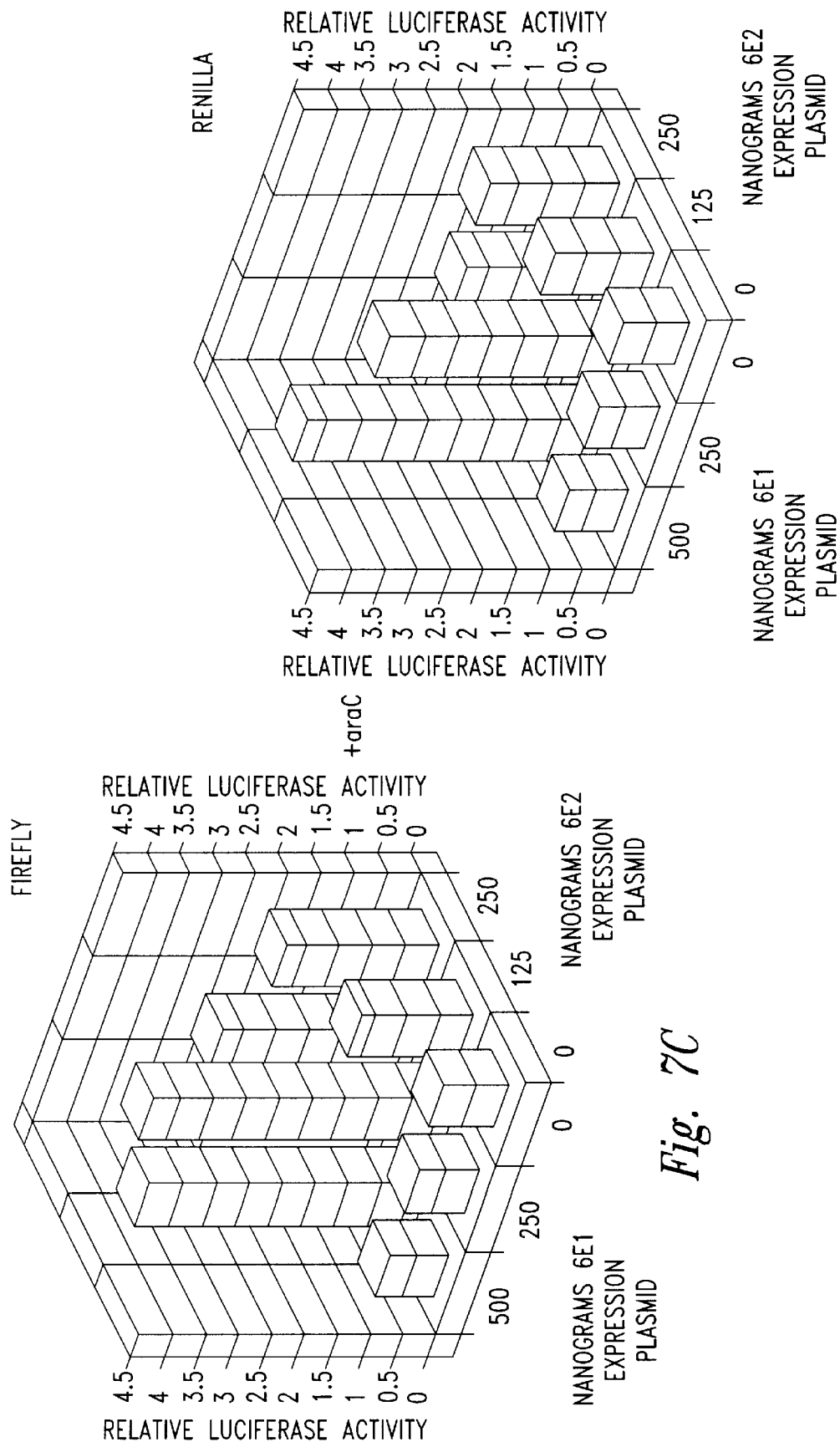

To further assess the effect of DNA replication on the stimulation of reporter gene expression by E1, an experiment was performed as described for FIGS. 4A and 4B, except that for two of the graphs shown (FIGS. 7C and 7D), cells were incubated in the presence of the replication inhibitor cytosine arabinoside (araC). The virtual elimination of E1 effects in the presence of araC indicates that stimulation of reporter gene expression in the presence of E1 is directly or indirectly dependent upon DNA replication.

From the foregoing, it will be appreciated that, although specific embodiments of the invention have been described herein for the purpose of illustration, various modifications may be made without deviating from the spirit and scope of the invention. Accordingly, the present invention is not limited except by the appended claims.

We claim:

1. A method for evaluating the ability of a protein to function as a transcriptional regulator and as a modulator of plasmid replication, comprising the steps of:
   (a) independently assaying levels of expression of a first reporter gene and a second reporter gene in a first host cell transformed or transfected with a dual reporter plasmid, wherein the dual reporter plasmid comprises:
      (i) the first reporter gene operably linked to a binding site for a transcriptional regulator such that transcription of the first reporter gene is modulated by the transcriptional regulator;
      (ii) the second reporter gene operably linked to a promoter such that transcription of the second reporter gene is not substantially modulated by the transcriptional regulator; and
      (iii) an origin of replication that comprises a binding site for a modulator of replication;
   and wherein the first host cell expresses a protein that is a candidate transcriptional regulator and a candidate modulator of plasmid replication; and
   (b) comparing the levels of expression of the first and second reporter genes determined in step (a) with predetermined levels of expression of the first and second reporter genes in a second host cell, wherein the second host cell is transformed or transfected with the dual reporter plasmid but does not detectably express the candidate protein, and therefrom evaluating the ability of the protein to function as a transcriptional regulator and as a modulator of plasmid replication.

2. A method according to claim 1, wherein the candidate transcriptional regulator and modulator of plasmid replication is a human papillomavirus (HPV) E1 or E2 protein.

3. A method according to claim 1, wherein the host cell is selected from the group consisting of keratinocytes and C33-A cells.

4. A method according to claim 1, wherein the first and second reporter genes encode different enzymes which are detected by a colorimetric, fluorometric and/or luminometric assay.

5. A method according to claim 4, wherein the first and second reporter genes are independently selected from the group consisting of firefly luciferase and Renilla luciferase.

6. A method for evaluating a first candidate agent and a second candidate agent for an ability to function as a transcriptional regulator and as a modulator of plasmid replication, comprising the steps of:
   (a) independently assaying levels of expression of a first reporter gene and a second reporter gene in a first host cell transformed or transfected with a dual reporter plasmid, wherein the dual reporter plasmid comprises:
      (i) the first reporter gene operably linked to a binding site for a transcriptional regulator such that transcription of the first reporter gene is modulated by the transcriptional regulator;
      (ii) the second reporter gene operably linked to a promoter such that transcription of the second reporter gene is not substantially modulated by the transcriptional regulator; and
      (iii) an origin of replication that comprises a binding site for a modulator of plasmid replication;
   and wherein the first host cell expresses the first and second candidate agents; and
   (b) comparing the level of expression of the first and second reporter genes determined in step (a) with predetermined levels of expression of the first and second reporter genes in a second host cell transformed or transfected with the dual reporter plasmid but that does not detectably express the first and second candidate agents, and therefrom evaluating the candidate agents for an ability to function as a transcriptional regulator and as a modulator of plasmid replication.

7. A method according to claim 6, wherein the candidate transcriptional regulator is a human papillomavirus E2 protein and wherein the candidate modulator of plasmid replication is a human papillomavirus E 1 protein.

8. A method according to claim 6, wherein the levels of expression of the first and second reporter genes are evaluated concurrently.

9. A method according to claim 6, wherein the host cell is selected from the group consisting of keratinocytes and C33-A cells.

10. A method according to claim 6, wherein the first and second reporter genes encode different enzymes which are detected by a colorimetric, fluorometric and/or luminometric assay.

11. A method according to claim 10, wherein the first and second reporter genes are independently selected from the group consisting of firefly luciferase and Renilla luciferase.

12. A method for screening for an agent that modulates gene expression and/or replication, comprising:
   (a) contacting a first host cell with a candidate agent, wherein the first host cell is transformed or transfected with a dual reporter plasmid, and wherein the dual reporter plasmid comprises:
      (i) a first reporter gene operably linked to a binding site for a transcriptional regulator such that transcription of the first reporter gene is modulated by the transcriptional regulator;
      (ii) a second reporter gene operably linked to a promoter such that transcription of the second reporter gene is not substantially modulated by the transcriptional regulator; and
      (iii) an origin of replication that comprises a binding site for a modulator of plasmid replication;
   and wherein the first host cell expresses a protein that is a transcriptional regulator and a modulator of plasmid replication;
   (b) independently assaying levels of expression of the first and second reporter genes; and
   (c) comparing the level of expression of the first and second reporter genes determined in step (b) with predetermined levels of expression of the first and second reporter genes in a second host cell that is not contacted with a candidate agent, wherein the second host cell is transformed or transfected with the dual reporter plasmid and expresses the protein that is a transcriptional regulator and a modulator of plasmid replication, and therefrom evaluating the ability of the candidate agent to modulate gene expression and plasmid replication.

13. A method according to claim 12, wherein the transcriptional regulator and modulator of plasmid replication is human papillomavirus E1 or E2 protein.

14. A method according to claim 12, wherein the levels of expression of the first and second reporter genes are evaluated concurrently.

15. A method according to claim 12, wherein the host cell is selected from the group consisting of keratinocytes and C33-A cells.

16. A method according to claim 12, wherein the first and second reporter genes encode different enzymes which are detected by a colorimetric, fluorometric and/or luminometric assay.

17. A method according to claim 16, wherein the first and second reporter genes are independently selected from the group consisting of firefly luciferase and Renilla luciferase.

18. A method for screening for an agent that modulates gene expression and/or replication, comprising:
   (a) contacting a first host cell with a candidate agent, wherein the first host cell is transformed or transfected with a dual reporter plasmid, and wherein the dual reporter plasmid comprises:
      (i) a first reporter gene operably linked to a binding site for a transcriptional regulator such that transcription of the first reporter gene is modulated by the transcriptional regulator ;
      (ii) a second reporter gene operably linked to a promoter such that transcription of the second reporter gene is not substantially modulated by the transcriptional regulator ; and
      (iii) an origin of replication that comprises a binding site for a modulator of plasmid replication;
   and wherein the first host cell expresses both a transcriptional regulator and a modulator of plasmid replication;
   (b) independently assaying levels of expression of the first and second reporter genes; and
   (c) comparing the level of expression of the first and second reporter genes determined in step (b) with predetermined levels of expression of the first and second reporter genes in a second host cell that is not contacted with a candidate agent, wherein the second host cell is transformed or transfected with the dual reporter plasmid and expresses the transcriptional regulator and the modulator of plasmid replication, and therefrom evaluating the ability of the candidate agent to modulate gene expression and plasmid replication.

19. A method according to claim 18, wherein the transcriptional regulator is a human papillomavirus E2 protein and wherein the modulator of plasmid replication is a human papillomavirus E1 protein.

20. A method according to claim 18, wherein the levels of expression of the first and second reporter genes are evaluated concurrently.

21. A method according to claim 18, wherein the host cell is selected from the group consisting of keratinocytes and C33-A cells.

22. A method according to claim 18, wherein the first and second reporter genes encode different enzymes which are detected by a colorimetric, fluorometric and/or luminometric assay.

23. A method according to claim 22, wherein the first and second reporter genes are independently selected from the group consisting of firefly luciferase and Renilla luciferase.

24. A dual reporter plasmid for use in a mammalian cell, comprising:
   (a) a first reporter gene operably linked to a binding site for a transcriptional regulator such that transcription of the first reporter gene is modulated by the transcriptional regulator;
   (b) a second reporter gene that is operably linked to a promoter such that transcription of the second reporter gene is not substantially modulated by the transcriptional regulator, wherein the second reporter gene encodes a protein having a measurable activity; and
   (c) an origin of replication that comprises a binding site for a modulator of plasmid replication.

25. A dual reporter plasmid according to claim 24, wherein the transcriptional regulator is a human papillomavirus E2 protein and wherein the modulator of plasmid replication is a human papillomavirus E1 protein.

26. A dual reporter plasmid according to claim 24, wherein the levels of expression of the first and second reporter genes may be evaluated concurrently.

27. A dual reporter plasmid according to claim 24, wherein the first and second reporter genes encode different enzymes which are detected by a colorimetric, fluorometric and/or luminometric assay.

28. A dual reporter plasmid according to claim 27, wherein the first and second reporter genes are independently selected from the group consisting of firefly luciferase and Renilla luciferase.

29. A host cell transformed or transfected with a dual reporter plasmid according to claim 24.

30. A dual reporter plasmid, comprising:
   (a) a first reporter gene operably linked to a binding site for a human papillomavirus E1 and/or E2 protein such that transcription of the first reporter gene is modulated by the human papillomavirus E1 and/or E2 protein;
   (b) a second reporter gene that is operably linked to a promoter such that transcription of the second reporter gene is not substantially modulated by a human papillomavirus E1 and/or E2 protein; and
   (c) an origin of replication that is bound by a human papillomavirus E1 protein.

31. A dual reporter plasmid according to claim 30, wherein the first and second reporter genes encode different enzymes which are detected by a colorimetric, fluorometric and/or luminometric assay.

32. A dual reporter plasmid according to claim 31, wherein the first and second reporter genes are independently selected from the group consisting of firefly luciferase and Renilla luciferase.

33. A host cell transformed or transfected with a dual reporter plasmid according to claim 30.

34. A host cell according to claim 33, wherein the cell is selected from the group consisting of keratinocytes and C33-A cells.

35. A method for screening for an agent that modulates human papillomavirus gene expression and/or replication, comprising:
   (a) contacting a candidate agent with a host cell transformed or transfected with a dual reporter plasmid according to claim 30, where in the host cell expresses human papillomavirus proteins E1 and E2;
   (b) independently as saying levels of expression of the first and second reporter genes; and
   (c) comparing the level of expression of the first and second reporter genes determined in step (b) with predetermined levels of expression of the first and second reporter genes in a second host cell that is not contacted with a candidate agent, wherein the second host cell is transformed or transfected with the dual reporter plasmid and expresses human papillomavirus proteins E1 and E2, and therefrom evaluating the ability of the candidate agent to modulate gene expression and plasmid replication.

36. A kit for evaluating an effect of an agent on gene expression and/or plasmid replication, comprising:
   (a) a cell line, wherein the cell line is transformed or transfected with a dual reporter plasmid according to claim 24 or claim 30; and
   (b) a supply of reagents for detecting expression of the first and second reporter genes.

37. A kit according to claim 36, wherein the cell line expresses human papillomavirus proteins E1 and E2.

38. A kit according to claim 36, wherein the first and second reporter genes encode enzymes which are detected by a colorimetric, fluorometric and/or luminometric assay.

39. A kit according to claim 38, wherein the first and second reporter genes are independently selected from the group consisting of firefly luciferase and Renilla luciferase.

40. A kit according to claim 36, wherein the cell line is selected from the group consisting of keratinocytes and C33-A cells.

* * * * *

SEQUENCE LISTING

<160> NUMBER OF SEQ ID NOS: 3

<210> SEQ ID NO 1
<211> LENGTH: 12

-continued

```
<212> TYPE: DNA
<213> ORGANISM: Human papillomavirus
<220> FEATURE:
<221> NAME/KEY: modified_base
<222> LOCATION: (4)..(9)
<223> OTHER INFORMATION: Where n indicates and independently selected
      nucleotide

<400> SEQUENCE: 1
accnnnnnng gt                                                              12

<210> SEQ ID NO 2
<211> LENGTH: 12
<212> TYPE: DNA
<213> ORGANISM: Human papillomavirus

<400> SEQUENCE: 2
accgaaaacg gt                                                              12

<210> SEQ ID NO 3
<211> LENGTH: 87
<212> TYPE: DNA
<213> ORGANISM: Artificial Sequence
<220> FEATURE:
<223> OTHER INFORMATION: Description of Artificial Sequence:  Positions
      7-93 containing four E2 binding sites of
      constructed Dual reporter Plasmid pDL-TK1
<220> FEATURE:
<221> NAME/KEY: protein_bind
<222> LOCATION: (1)..(12)
<223> OTHER INFORMATION: E2 binding sequence
<220> FEATURE:
<221> NAME/KEY: protein_bind
<222> LOCATION: (16)..(27)
<223> OTHER INFORMATION: E2 binding sequence
<220> FEATURE:
<221> NAME/KEY: protein_bind
<222> LOCATION: (61)..(72)
<223> OTHER INFORMATION: E2 binding sequence
<220> FEATURE:
<221> NAME/KEY: protein_bind
<222> LOCATION: (76)..(87)
<223> OTHER INFORMATION: E2 binding sequence

<400> SEQUENCE: 3
accgaaaacg gttcaaccga aaacggtccc gggaggtacc gagctcttac gcgtgctagc          60
accgaaaacg gttcaaccga aaacggt                                              87
```